US00PP08378P

United States Patent [19]

Vardi et al.

[11] Patent Number: Plant 8,378

[45] Date of Patent: Sep. 14, 1993

[54] MANDARIN TREE NAMES MOR

[75] Inventors: Aliza Vardi; Pinchas Spiegel-Roy, both of Ramat Gan; Avraham Elchanati, Holon, all of Israel

[73] Assignee: State of Israel-Ministry of Agriculture, Bet Dagan, Israel

[21] Appl. No.: 763,394

[22] Filed: Sep. 20, 1991

[51] Int. Cl.[5] ..... A01H 5/00

[52] U.S. Cl. ..... Plt./45

[58] Field of Search ..... Plt./45

*Primary Examiner*—James R. Feyrer

*Attorney, Agent, or Firm*—Browdy and Neimark

[57] ABSTRACT

A new variety of mandarin citrus distinguished by fruit having few seeds, flowers having anthers bearing pollen with low pollen fertility, and a growth habit wherein the trees are short and compact.

1 Drawing Sheet

FIELD OF THE INVENTION

This invention is directed to a novel variety of mandarin tree of the genus Citrus L. which resulted from a selection of plants grown from irradiated budwood of cv Murcott, made at the Agricultural Research Organization, the Volcani Center, Bet Dagan, Israel.

BACKGROUND OF THE INVENTION

The objective in breeding the present novel variety, assigned the denomination MOR, was to obtain a late ripening mandarin citrus wherein the fruit has few seeds.

The breeding program of the Agricultural Research Organization, the Volcani Center, Bet Dagan, Israel includes, in addition to performing various cross pollinations, inducing seedlessness by mutation breeding in easy peeling varieties.

In the spring of 1985 about 400 buds of an easy peeling mandarin cultivar, Murcott, was irradiated at the Nahal Soreq Nuclear Center, Yavne, Israel, by exposure to 35 kh of gamma radiation from a $^{60}Co$ source. Sour Orange nucellar rootstocks were bud grafted with the individual buds of irradiated Murcott budwood and labeled $mV_1$. Six to nine months after grafting the irradiated budwood, individual buds from the $mV_1$ plants were regrafted on Sour Orange nucellar rootstocks to establish about 700 $mV_2$ plants.

Field plantings were established from container grown $mV_2$ plants in the spring of 1987. The first fruits were observed in January–February 1989 and a second observation of the fruits was made in January to February 1990.

One of the selections, which was designated 13/24, had medium to large sized orange colored fruit, and was easy to peel. This selection was distinguished from Murcott by the following features.

The selection 13/24 was a compact tree. During the four years after being transplanted to the grove it was consistently ⅓ to ½ the size of Murcott.

Selection 13/24 had fruit with few seeds. Typically, this selection had fruit with 5–7 seed per fruit as compared with 20–25 seeds per fruit for Murcott.

Selection 13/24 has flowers with low pollen fertility. Typically, 28–30% of the pollen grains of selection 13/24 were stained by acetocarmine as compared with 95% staining for Murcott.

The occurence of a favorable selection such as '13/24' from a limited population was surprising since the mutation frequency would be expected to be low, about one in 10,000 to about 1 in 100,000 and deleterious mutations can also occur.

SUMMARY OF THE INVENTION

The present invention provides a novel variety of mandarin citrus characterized by a small sized tree, fruit with few seeds, flowers having anthers bearing pollen with low fertility and a tree which is smaller in size than trees of the cv Murcott.

BRIEF DESCRIPTION OF THE DRAWINGS

Distinctive characteristics of the new variety are exemplified in the accompanying illustrations in which.

PLANT CHARACTERISTICS

Figure 2:
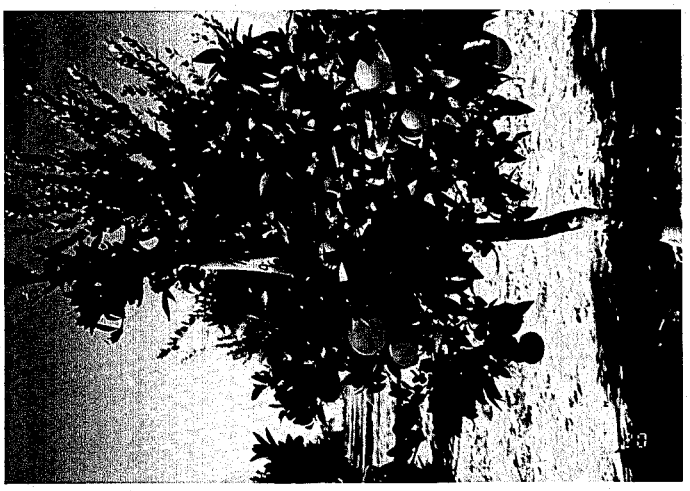
FIG. 2 shows the tree and the leaf canopy of the new variety.
Figure 1:
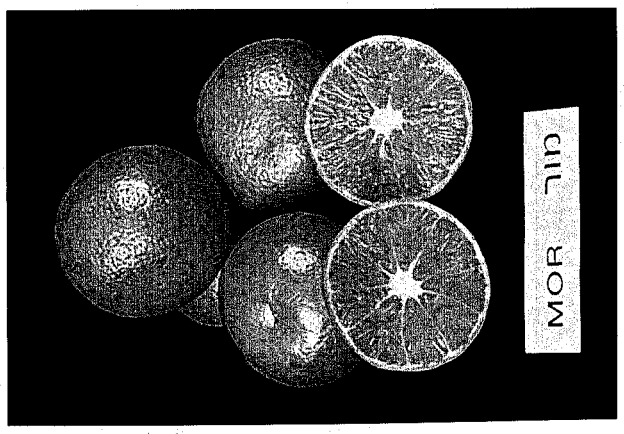
FIG. 1 shows whole fruit of the new variety illustrating the exterior of the fruit, as well as traverse mid-sections of the fruit in a plane substantially perpendicular to the axis of the fruit, illustrating few seeds in interior of the fruit.

The following is a detailed description of the new mandarin citrus variety based on observations made under typical Israeli grove conditions.

Tree: The tree shape and fruit appearance is similar to that of Murcott but the tree is about half the size, approximately 1.5 meters at maturity as compared with approximately 3.0 meters for Murcott. The vigor of the tree is about the same as that of the parent Murcott with a growth after pruning of 50 cm to 60 cm as measured between April and November in Bet Dagan, Israel in 1991. The tree is basally dominant, however, after pruning the newly formed branches grow upright. The chromosome number from the morphological characteristics of the tree is assumed to be the same as the parent $2n=18$. Water shoots are thorny. Small thorns, 1 mm to 3 mm are usually present in the leafy part of branches especially in their lower portion and on the lower part of fruit bearing branches. Main branches have an upright attitude and young shoots have no anthocyanin coloration at the tip.

The bearing of the tree is regular and the productivity is relatively high, about the same as for Murcott despite the smaller size of the tree. The canopy is moderately dense and there is little tendency to form water sprouts from scions. The bark of the young tree is initially smooth and green gradually turning into a smooth brown-gray.

Leaf: The leaves are similar to that of Murcott. They are small to medium in size, lanceolate, and sharp pointed. Leaf blades are firm, without undulation and concave in cross section. Petioles are without wings or have rudimentary wings.

Flower: The characteristics of flowering and of the flower parts are similar to those of Murcott. Flowering for both occurs in April as measured in Bet Dagan, Israel in 1991.. Both Mor and Murcott product about the same number of flowers and flower drop for both occurs in June. Terminal flower buds have no anthocyanin coloration. Flowers are borne singly and have an average number of stamens (about 20) with complete style development. Anther color is pale yellow with viable pollen present, however pollen fertility is low as indicated by the observation that only 28–30% of the pollen grains were stainable with acetocarmine in a test conducted at the Agricultural Research Organization. The Volcani Center as compared with a stainability of about 86% for Murcott pollen grains. Vestigial and/or aborted seeds are seen only occasionally in mature fruits.

Fruit: The fruit has few seeds, about 2 to 7 seeds, even when optimal pollination conditions are employed. This compares with about 25 seeds per fruit in Murcott. In other respects the fruit characteristics are in the range of the parent cv Murcott. The fruit shape is oblate and it is medium sized. When 50 fruits were measured, the fruit had an average weight 120 grams, an average height 45–55 mm, and an average diameter 55–68 mm. The fruit has a moderately depressed stalk end and a truncate distal end. The fruit surface is smooth with a yellow orange color, 21B on The Royal Horticultural Society of London Colour Chart, and bears an average number of conspicuous rind oil glands. Fruit color and ripening of the fruit do not differ from the outside of the canopy to the inside. There is no persistance of the style and an areola is present but not completely developed. A navel is absent or very rare. The rind is thin and the flesh shows a medium adherence to the rind.

The color of the albedo is white and the flesh is mainly orange in color. The columella is solid and of average diameter. The fruit contains 9–11 segments and is very juicy. The external color of the seed is ivory both when fresh and when dry. The internal seed coat is white and so are the cotyledons. Polyembryonic seeds are present and over 50% of the seed are polyembronic. The seed size, shape, texture, and polyembrony are similar to that of the parent Murcott. The fruit reaches maturity late in the growing season as does Murcott which in Bet Dagan, Israel in 1991 was in mid-February. The ripening of the fruit on the tree and within the fruit is uniform. Fruit remaining on the tree does not regreen or puff and does begin to loose quality until April. If the tree is not picked before April, however, it becomes alternate bearing. Preharvest drop of both developed and underdeveloped fruit is similar to that of the parent cv Murcott.

The results of a test conducted Mar. 3, 1991 on juice of representative ripe fruit of the novel variety are as follows:

Total soluble solids (TSS): 15.5%.
Acid content: 1.28%.
TSS/acid ratio: 12.1.

The juice has a juicy, rich flavor.

We claim:

1. A novel variety of mandarin citrus substantially as herein shown and described, characterized by having about 2–7 seeds per fruit, flowers having anthers bearing pollen with low pollen fertility and a tree which is smaller in size than trees of cv Murcott.

* * * * *